(12) United States Patent
Morris et al.

(10) Patent No.: US 7,714,297 B2
(45) Date of Patent: May 11, 2010

(54) PARTICLE DETECTION SYSTEMS AND METHODS

(75) Inventors: Christopher L. Morris, Los Alamos, NM (US); Mark F. Makela, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/977,314

(22) Filed: Oct. 24, 2007

(65) Prior Publication Data

US 2008/0099691 A1     May 1, 2008

Related U.S. Application Data

(60) Provisional application No. 60/855,064, filed on Oct. 27, 2006.

(51) Int. Cl.
    *G01J 1/42*      (2006.01)
(52) U.S. Cl. ...................................................... 250/393
(58) Field of Classification Search ................. 250/393
See application file for complete search history.

(56) References Cited

U.S. PATENT DOCUMENTS

| | | | | |
|---|---|---|---|---|
| 4,241,253 | A * | 12/1980 | Allen et al. | 250/390.01 |
| 4,599,515 | A | 7/1986 | Whittemore | 250/390 |
| 7,470,905 | B1 | 12/2008 | Goldberg et al. | |
| 2005/0205798 | A1* | 9/2005 | Downing et al. | 250/390.11 |
| 2006/0180753 | A1 | 8/2006 | Bryman | 250/266 |
| 2006/0284094 | A1* | 12/2006 | Inbar | 250/359.1 |
| 2007/0102648 | A1 | 5/2007 | Shpantzer et al. | |

OTHER PUBLICATIONS

Alexopoulos et al., "Measurement of the monitored drift tubes response to energetic neutrons,", 2004, IEEE Tranacitions on Nuclear Science, vol. 51, No. 5, pp. 2448-2452.*
Markoff et al., "evelopment of a position sensitive neutron detector with high efficiency and energy resolution for use at high-flux beam sources", 2005, Journal of Research of the National Institute of Standards and Technology, vol. 110, No. 4, pp. 449-452.*

(Continued)

*Primary Examiner*—David P Porta
*Assistant Examiner*—Kiho Kim
(74) *Attorney, Agent, or Firm*—Kermit D. Lopez; Luis M. Ortiz; Matthew F. Lambrinos

(57) ABSTRACT

Techniques, apparatus and systems for detecting particles such as muons and neutrons. In one implementation, a particle detection system employs a plurality of drift cells, which can be for example sealed gas-filled drift tubes, arranged on sides of a volume to be scanned to track incoming and outgoing charged particles, such as cosmic ray-produced muons. The drift cells can include a neutron sensitive medium to enable concurrent counting of neutrons. The system can selectively detect devices or materials, such as iron, lead, gold, uranium, plutonium, and/or tungsten, occupying the volume from multiple scattering of the charged particles passing through the volume and can concurrently detect any unshielded neutron sources occupying the volume from neutrons emitted therefrom. If necessary, the drift cells can be used to also detect gamma rays. The system can be employed to inspect occupied vehicles at border crossings for nuclear threat objects.

27 Claims, 12 Drawing Sheets

OTHER PUBLICATIONS

Alexopoulous et al., "Investigation of the ATLAS MDT chambers response to Fast neutron background radiation," 2004, IEEE, Nuclear Science Symposium Record, vol. 1, pp. 667-671.*

A Terrorist Threat—The Movement of Black Market Nuclear Materials into the United States; Gene R. Kelley, Nov. 17, 2001; www.wagingpeace.org/articles/2001/11/17_kelley_terrorist-threat.htm.

Radiographic Imaging with Cosmic-Ray Muons; K.N. Borozdin, G.E. Hogan, C. Morris, W.C. Priedhorsky, A. Saunders, L.J. Schultz, M.E. Teasdale; Los Alamos National Laboratory; vol. 422, Mar. 20, 2003, www.nature.com/nature.

Detection of High-Z Objects Using Multiple Scattering of Cosmic Ray Muons; W.C. Priedhorsky, K.N. Borozdin, G.E. Hogan, C. Morris, A. Saunders, L.J. Schultz, M.E. Teasdale; Review of Scientific Instruments, vol. 74, No. 10, Oct. 2003.

Cosmic Ray Muon Radiography; Larry J. Schultz; Dissertation for Ph.D. Electrical and Computer Engineering, Portland State University 2003.

Image Reconstruction and Material Z Discrimination Via Cosmic Ray Muon Radiography; L.J. Schultz, K.N. Borozdin, J.J. Gomez, G.E. Hogan, J.A. McGill, C.L. Morris, W.C. Priedhorsky, A. Saunders, M.E. Teasdale; NIM Submission Draft—Jun. 30, 2003.

Borozdin, Konstantin et al., "Cosmic-Ray Muon Tomography and Its Application to the Detection of High-Z Materials", Proceedings of the 46th Annual Meeting, Institute of Nucelar Materials Management, 2005, pp. 1-8.

Van Eijik, Carl W.E., "Neutrons PSD's for the Next Generation of Spallation Neutron Sources" Nuclear Instruments and Methods in Physics Research A, 2002, vol. 477, pp. 383-390.

Zhao, T. et al. "D0 Forward-Angle Muon Tracking Detector and Its Gas System", IEEE Transactions on Nuclear Science, Jun. 2002, vol. 49, No. 3 pp. 1092-1096.

Byrd, Roger C. et al. "Nuclear Detection to Prevent or Defeat clandestine Nuclear Attack", IEEE Sensors Journal, Aug. 2005, vol. 5, No. 4, pp. 593-609.

Zhou, Bing, "Large Precision Muon Detector for ATLAS", Nuclear Instruments and Methods in Physics Research A, 2002, vol. 494, pp. 464-473.

Hengartner, Nicolas et al., Information Extraction for Muon Radiography, Nuclear Science Symposium Conference Record, 2005 IEEE vol. 1, Oct. 23-29, 2005, pp. 11-15.

Fessler, Jeffrey A. "Statistical Methods for Image Reconstruction" (annotated slides for attendees of the NSS-MIC short Course), Oct. 24, 2004.

Schultz, L. J. et al., "Image Reconstruction and Material Z Discrimination via Cosmic Ray Muon Radiography", Nuclear Instruments and Methods in Physics Research A, 2004, vol. 519, pp. 687-694.

Jenneson, P.M. "Large Vessel Imaging Using Cosmic-ray Muons", Nuclear Instruments and Methods in Physics Research A, 2004, vol. 525, pp. 346-351.

Fessler, Jeffery A., "Penalized Maximum-Likelihood Image Reconstruction Using Space-Alternating Generalized EM Algorithms", IEEE Transactions on Image Processing, 1995, vol. 4 No. 10, pp. 1417-1429.

PCT—Notification of Transmittal of the International Search Report and the Written Opinion of the International Searching Authority, or the Declaration, Date of Mailing, Dec. 24, 2008.

* cited by examiner

Uranium among automobile differentials

Fan beam 8 MV simulation $$\Delta l = \frac{\lambda}{\sqrt{N}}$$

$$\lambda \approx 120 \text{ cm}$$

$$\frac{\Delta l}{l} \approx 1.2$$

| Material | dE/dx | χ |
|----------|-------|---|
|  | MeV-cm$^2$/gm | cm |
| $H_2O$ | 2.06 | 36 |
| Fe | 1.87 | 1.76 |
| Pb | 1.54 | 0.56 |

*FIG. 10*

PARTICLE DETECTION SYSTEMS AND METHODS

CROSS-REFERENCE TO PROVISIONAL APPLICATION

This application claims priority under 35 U.S.C §119(e) to the U.S. provisional patent application No. 60/855,064, entitled "Systems, Methods and Apparatus for Particle Detection and Analysis and Field Deployment of the Same", which was filed Oct. 27, 2006, the disclosure of which is incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to particle detection systems and methods for use at ports and border crossings.

BACKGROUND OF THE INVENTION

The threat of the detonation of a nuclear device in a major US city has prompted research aimed at providing more robust border surveillance for contraband nuclear material.

An article entitled "A Terrorist Threat—The movement of Black Market Nuclear Materials into the United States" dated November 2001 in the name of Gene R. Kelley from the article archives of the Nuclear Age Peace Foundation, PMB 121, 1187 Coast Village Road, Suite 1, Santa Barbara, Calif. 93108, USA outlines the problem of surreptitious transport of special nuclear material. Kelly refers to some possibilities for moving this type of material as being as follows:

1) —superimpose the shipment of small, well-shielded packages on established drug and contraband routes.

2) —ship materials conventionally in well shielded, small containers through a surreptitiously network of widely dispersed handlers.

3) —man carrying many small quantities across the mostly porous borders of the United States.

4) —use diversified distribution techniques (routes and conveyances) by requiring multiple way-points and altering the characteristics of external shipping containers at each point.

5) —mix materials and legitimate products for routine deliveries.

Kelley concludes that the formidable nature of the tasks required to detect and identify well packaged fissile materials renders the likelihood of detection of small quantities highly questionable.

The use of portal monitors at border crossing points is becoming routine for detecting smuggled nuclear materials. In many cases shielding can be used to obscure a nuclear signature. Conventional nuclear material detectors use high resolution gamma or X ray detectors.

Unshielded Kg quantities of highly enriched uranium can be detected with high reliability with 1 minute counting times by detecting gamma rays from the 238 U impurity. FIG. 1 of the accompanying drawings depicts example count data from a high resolution gamma ray detector used to detect a depleted uranium target: 10% 238 U 90% 235 U without shielding and with 5 cm and 2.5 cm of lead shielding, respectively. FIG. 1 indicates how self-shielding of nuclear material reduces count rates. In order to shield a threat object, about 5 cm thick lead, gold, tungsten, or other shielding material is required.

As indicated by FIG. 1 and additionally FIGS. 2 & 3, which illustrate simulations of X-radiography of 20 kg of uranium among automobile differentials using a fan beam of x-rays generated by an 8 MeV electron bremsstrahlung source. These simulations show that X-ray radiography can visualize objects, even in some dense, cluttered cargo, but definitive signatures of high z objects are confused by scatter backgrounds and transmission is insufficient for many cargos.

Having regard to the foregoing, the small amount of material needed to construct a nuclear device and the ease with which neutron and gamma ray signatures can be obscured with shielding makes robust border surveillance for contraband nuclear material difficult.

BRIEF SUMMARY

The following summary of the invention is provided to facilitate an understanding of some of technical features related to techniques, apparatus and systems for detecting particles such as muons and neutrons that are described in this application and is not intended to be a full description. A full appreciation of the various aspects of the invention can be gained by taking the entire specification, claims, drawings, and abstract as a whole.

Techniques, apparatus and systems for detecting particles such as muons and neutrons are described in various examples. In one implementation, a particle detection system is disclosed to employ a plurality of drift cells, which can be for example sealed gas-filled drift tubes, arranged on sides of a volume to be scanned to track incoming and outgoing charged particles, such as cosmic ray muons. The drift cells can include a neutron sensitive medium, such as a partial pressure of neutron sensitive operating gas or a layer of neutron sensitive material disposed in the interior of the drift cells, to enable concurrent counting of neutrons. The system can selectively detect devices or materials, such as iron, lead, gold uranium, plutonium and/or tungsten, occupying the volume from multiple scattering of the charged particles passing through the volume and can concurrently detect any unshielded neutron sources occupying the volume from neutrons emitted therefrom. If necessary, the drift cells can be used to also detect gamma rays. The system can be employed to inspect occupied vehicles at border crossings for nuclear threat objects.

The aforementioned aspects of the invention and other objectives and advantages can now be achieved as described herein.

According to one aspect, a particle detection system has a charged particle tracker having a plurality of particle detectors. The particle detectors can comprise drift cells arranged on sides of a volume to be scanned to enable tracking of incoming and outgoing charged particles passing through the volume. At least some of the drift cells can comprise neutron sensitive drift cells which include a neutron sensitive medium to enable concurrent detection of neutrons. In use, the system can both selectively detect any materials or devices, especially of high density, occupying the volume from multiple scattering of the charged particles and concurrently detect any unshielded neutron sources occupying the volume from neutrons emitted therefrom.

The charged particle tracker can be a cosmic ray-produced charged particle tracker. Adopting a charged particle tracker with drift cells configured to track cosmic ray-produced charged particles and concurrently detect neutrons enables detection of shielded and unshielded nuclear material using a single detector system. The system is capable of determining if a given vehicle or cargo is free of nuclear threats by both measuring the absence of a potential shielded package and the absence of a radiation signature. The particle detector system is more compact and cost effective and can be used to look for nuclear devices and materials at border crossings and ports.

The neutron sensitive medium can comprise a neutron sensitive solid material or gas. The neutron sensitive medium can comprise, for example, helium-3 (3He)), boron, a compound of boron, or lithium or a compound of lithium can be in solid, liquid or gas form. Boron may be enriched in the neutron-absorbing isotope Boron-10 and Lithium in the neutron-absorbing isotope Lithium-6. A hydrogenous material, such as polyethylene, paraffin, other hydrogenous organic material, or water, can be used to enclose the neutron sensitive drift cells thereby causing the neutron particles to pass through the drift cells multiple times and to be isolated from the material or devices being scanned. The hydrogenous material can be carried on the exterior and/or interior of the system such that neutrons are trapped and reflected towards the neutron sensitive drift cells.

The drift cells on each of the sides can be arranged to allow at least three charged particle positional measurements in a first direction and at least three charged particle positional measurements in a second direction different from the first direction. For example, the drift cells on each of the sides can comprise three sets of drift tube detectors having drift tube modules disposed in generally orthogonal directions. The hydrogenous material can enclose neutron sensitive drift tubes of middle sets of drift cell detectors.

The drift cells can also be adapted to carry either or both of a gamma ray scattering gas and gamma ray scattering solid material to also enable detection of compton scattered electrons from gamma interactions such that, in use, the system can additionally detect any radioactive sources occupying the volume from gamma rays emitted therefrom.

The drift cells can be further adapted and arranged on surrounding sides of the volume such that the drift cells form a box or four sided structure into which a vehicle or cargo container can enter for scanning by the system.

According to another aspect, a particle detection system for ports and border crossings has a cosmic ray muon tracker having a plurality of muon detectors. The muon detectors can comprise drift cells, such as aluminum gas-filled drift tubes (e.g. aluminum tubes), arranged at least above and below a volume to be scanned to enable tracking of incoming and outgoing muons. At least some of the drift cells can comprising neutron sensitive drift cells can include a neutron sensitive medium, such as helium, a boron compound such as boron-trifluoride, lithium compound or lithium, to enable counting of neutrons. Boron may be enriched in boron-10 and lithium in lithium-6. In use, the system can selectively detect any shielding or other objects occupying the volume from multiple scattering of the muons passing through the volume and concurrently detect any neutron sources occupying the volume from neutrons emitted therefrom.

The particle detection system can be used for inspecting occupied vehicles at border crossings for nuclear threat objects that may range from fully assembled nuclear weapons to small quantities of highly shielded nuclear materials.

The drift tubes can be arranged above the volume comprise at least three drift tubes configured in a first direction and another at least three drift tubes configured in a second direction, optionally orthogonal to the first direction, and wherein the drift tubes arranged below the volume comprise at least three drift tubes configured in a first direction and another at least three drift tubes configured in a second direction, optionally orthogonal to the first direction.

The neutron sensitive medium included in the neutron sensitive gas-filled drift tubes can comprise a partial pressure of neutron sensitive gas and/or a layer of neutron sensitive material disposed in the interior of the drift tubes. Including a partial pressure of Helium-3 (3He) or other neutron sensitive gas provides efficient selective neutron detection with no impact on muon tracking.

A hydrogenous material can enclose at least some of the neutron sensitive drift tubes thereby causing the neutrons to pass through the neutron sensitive drift tubes multiple times and to be isolated from the material or devices being scanned. Enclosing the neutron sensitive drift tubes in hydrogenous material increases coverage and neutron detection efficiency of the particle detection system.

The drift tubes can be fabricated from aluminum or another gamma ray compton scattering, electron producing material. The operating gas of the drift tubes can also comprise a gamma ray compton scattering, electron producing gas. Adopting gamma ray compton scattering material in the drift tube and/or operating gas enhances the system's ability to additionally detect any radioactive sources occupying the volume from gamma rays emitted therefrom.

According to another aspect, a method of particle detection comprises arranging a plurality drift cells on sides of a volume to be scanned; detecting with the drift cells incoming and outgoing cosmic ray-produced charged particles; adding a neutron sensitive medium to the drift cells to enable concurrent detection of neutrons; selectively detecting any high density material occupying the volume from multiple scattering of the charged particles passing through the volume; and detecting any neutron sources occupying the volume from detection of the neutrons.

Arranging a plurality of drift cells on sides of a volume to be scanned can comprise arranging a plurality of gas-filled drift tubes on the sides of the volume; and wherein adding a neutron sensitive medium to the drift cells comprises adding a partial pressure of neutron sensitive gas to the operating gas of the gas-filled drift tubes and/or disposing a layer of neutron sensitive material in the gas-filled drift tubes.

According to yet another aspect, a neutron sensitive drift tube for use in a combined charged particle and neutron detection system has an operating gas selected to enable tracking of charged particles, such as cosmic ray produced charged particles, and has a neutron sensitive medium disposed therein to enable concurrent detection of neutrons. The neutron sensitive medium can comprise a partial pressure of neutron sensitive gas and/or a layer of neutrons sensitive material disposed in the drift tube. The neutron sensitive medium can comprise helium-3 (3He), boron or lithium. Natural boron may be enriched in boron-10 and natural lithium enriched in lithium-6.

In yet another aspect, a particle detection system is disclosed to include a first set of particle detectors located on a first side of an object holding area to measure incident cosmic ray-produced charged particles, such as muons, towards the object holding area and to respond to a neutron to measure neutrons; and a second set of particle detectors located on a second side of the object holding area opposite to the first side to measure outgoing cosmic ray-produced charged particles exiting the object holding area and to respond to a neutron to measure neutrons. Each particle detector comprises a cosmic ray-produced charged particle sensitive material to measure cosmic-ray produced charged particles and a neutron sensitive material to measure neutrons and is operable to simultaneously measure both cosmic-ray produced charged particles, and neutrons.

In one implementation of the above system, each particle detector comprises a drift tube filled with a mixture of a muon sensitive gas and a neutron sensitive gas, each of the first and second sets of particle detectors is configured to be a set of position sensitive detectors to measure positions and directions of received muons, and the system comprises a signal processing unit to process measured signals from the first and second sets of particle detectors to produce a tomographic profile of one or more objects in the object holding area.

In yet another aspect, a particle detection system is described to include a first set of position sensitive muon detectors located on a first side of an object holding area to measure positions and directions of incident muons towards the object holding area, a second set of position sensitive muon detectors located on a second side of the object holding area opposite to the first side to measure positions and directions of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. This signal processing unit is configured to analyze scattering behaviors of the muons caused by scattering of the muons in the materials within the object holding area based on the measured incoming and outgoing positions and directions of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray-produced muons as the source of muons for detecting one or more objects in the object holding area.

In yet another aspect, a particle detection system has a plurality of particle detectors comprising drift cells including a neutron sensitive medium, such as helium-3 (3He), boron or lithium, to enable detection of neutrons. The neutron sensitive drift cells are arranged on sides of a volume to be scanned to enable detection of neutrons emitted within that volume. Hydrogenous material surrounding the neutron-sensitive cells can be provided to moderate and trap the neutrons.

The neutron sensitive medium can be a partial pressure of neutron sensitive gas in drift cells or a solid neutron sensitive material carried on or in the inner walls of the drift cells. A hydrogenous material can enclose the neutron sensitive drift cells thereby causing the neutrons to be thermal zed in energy, to pass through the drift cells multiple times and to be isolated from the material or devices being scanned.

The hydrogenous material can comprise polyethylene, other organic hydrogenous material, or water. The hydrogenous material can be carried on the exterior and/or interior of the system such that neutrons are reflected towards the neutron sensitive drift cells and are trapped.

The drift cells can also carry a gamma ray compton scattering electron producing gas and/or solid to enable detection of gamma rays such that, in use, the system can additionally detect gamma rays emitted therefrom.

The drift cells can be further adapted and arranged on surrounding sides of the volume such that the drift cells form a box or four sided structure.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 10 depicts a table showing theoretical energy loss rate (dE/dx) and radiation length (X) for various material;

DETAILED DESCRIPTION

Figure 1:
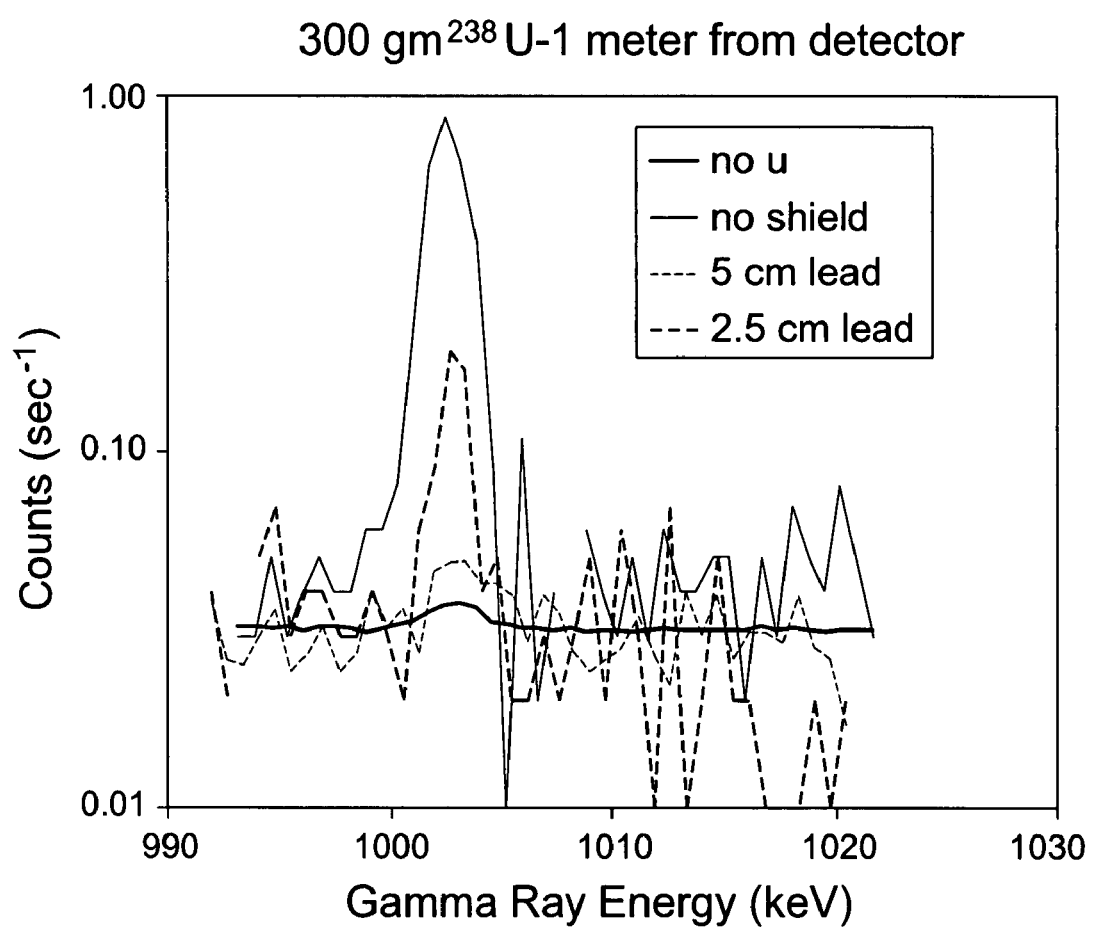
FIG. 1 illustrates example count data from a high resolution gamma ray detector used to detect Weapon grade uranium (WGU) or highly enriched uranium (HEU): 10% 238 U 90% 235 U, using the gamma-ray signal from a 400 gm sample of 238 U, without shielding and with 5 cm and 2.5 cm of lead shielding, respectively.
Figure 2:
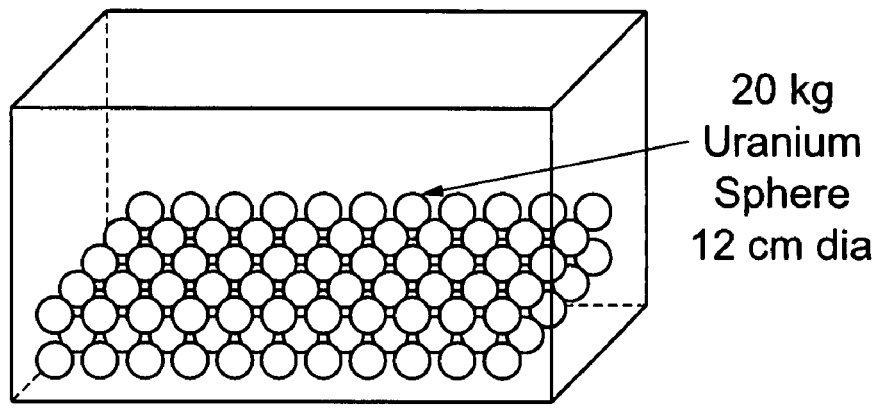
FIGS. 2 and 3 illustrate X-ray radiography simulations of uranium detection among automobile differentials and a fan beam produced by bremsstrahlung of 8 MeV electrons on a tungsten target.
Figure 3:
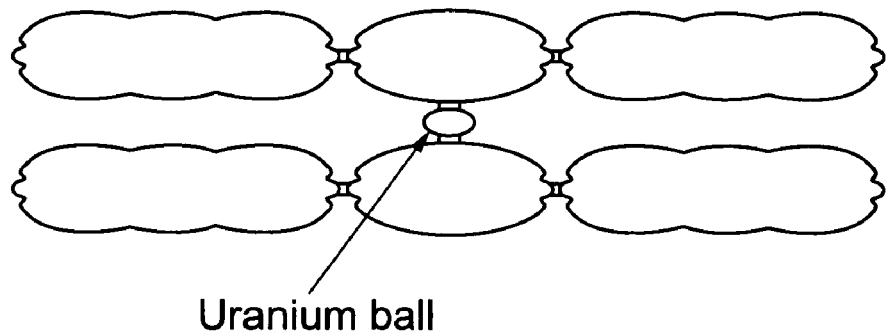

The particular values and configurations discussed in these non-limiting examples can be varied and are cited merely to illustrate at least one embodiment of the present invention and are not intended to limit the scope of the invention.

The particle detection system and methods described in this application can be implemented to detect presence of certain objects or materials such as nuclear materials and to obtain tomographic information of such objects in various applications including but not limited to inspecting, packages, containers, occupied vehicles at security check points, border crossings and other locations for nuclear threat objects that may range from fully assembled nuclear weapons to small quantities of highly shielded nuclear materials. The approach enables detection of shielded and unshielded nuclear material using a single detector system in a compact configuration to provide a cost effective detector way for detecting nuclear devices and materials.

Features described in this application can be used to construct various particle detection systems. For example, a particle detection system can include an object holding area for placing an object to be inspected, a first set of position sensitive muon detectors located on a first side of the object holding area to measure positions and directions of incident muons towards the object holding area, a second set of position sensitive muon detectors located on a second side of the object holding area opposite to the first side to measure positions and directions of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by scattering of the muons in the materials within the object holding area based on the measured incoming and outgoing positions and directions of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray-produced muons as the source of muons for detecting one or more objects in the object holding area.

Another example of a particle detection system based on features described in this application can include an object holding area for placing an object to be inspected, a first set of particle detectors located on a first side of the object holding area to measure incident muons towards the object holding area and to respond to a neutron to measure neutrons, and a second set of particle detectors located on a second side of the object holding area opposite to the first side to measure outgoing muons exiting the object holding area and to respond to a neutron to measure neutrons. Each particle detector includes a muon sensitive material to measure muons and a neutron sensitive material to measure neutrons and is operable to simultaneously measure both muons and neutrons. This system includes a signal processing unit to receive and process data of measured signals from the first and second sets of detectors to produce a measurement of one or more objects in the object holding area. In one implementation, each particle detector can be a drift tube filled with a mixture of a muon sensitive gas and a neutron sensitive gas and operates as a position sensitive detector. Each set of particle detectors can be designed as a set of position sensitive detectors to measure positions and directions of received muons. For example, each of the first and second sets of particle detectors can be implemented to include drift tubes arranged to allow at least three charged particle positional measurements in a first direction and at least three charged particle positional measurements in a second direction different from the first direction. The signal processing unit can be configured to obtain tomographic profile or the spatial distribution of the material of one or more objects in the object holding area such as materials with high atomic numbers including nuclear materials or devices. Such a system can be used to utilize natural cosmic ray-produced muons as the source of muons for detecting one or more objects in the object holding area. In some applications, such a system can be configured to use one or more artificial sources of particles to produce the muons or neutrons for detecting one or more objects in the object holding area.

The particle detection systems of the illustrative embodiments shown in the accompanying drawings employ drift cells to detect charged particles and/or neutron particles. Advantageously, these particle detection systems can be used as an efficient monitor for radiation emitted from threat objects.

As will be explained in more detail below, in particular illustrative embodiments, the particle detection systems can utilize drift tubes to enable tracking of charged particles, such as muons, passing through a volume as well as concurrent detection of neutron particles. However, those skilled in the art would understand that such charge particle detectors can be employed in applications other than cosmic ray-produced charged particle tracking to detect charged particles other than cosmic ray-produced charged particles. These charged particle detectors are applicable to any charged particle from any appropriate source. For example, muons can be produced by cosmic rays or a low intensity beam of muons from an accelerator.

Cosmic ray tomography is a technique which exploits the multiple Coulomb scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. They lose energy only slowly through electromagnetic interactions. Consequently, many of the cosmic ray-produced muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (such as lead and tungsten for example) and by special nuclear material (SNM), that is, uranium and plutonium, than by materials that make up more ordinary objects such as water, plastic, aluminum and steel. Each muon carries information about the objects that it has penetrated, and by measuring the scattering of multiple muons one can probe the properties of these objects. a material with a high atomic number Z and a high density can be detected and identified when the material is located, inside low-Z and medium-Z matter.

Coulomb scattering from atomic nuclei results in a very large number of small angle deflections of charged particles as the transit the matter. Enrico Fermi found and solved a transport equation that describes this process to a good approximation. The result is a correlated Gaussian distribution function for the displacement and angle change of the trajectory that depends on the density and the atomic charge of the material. The width of the distribution function is proportional to the inverse of the momentum of the particle and the square root of the real density of material measured in radiation lengths. Further background can be found in the reference of K. N Borozdin et al entitled "Surveillance: Radiographic Imaging with Cosmic Ray Muons", published in Nature (2003), 422,277.

Cosmic ray-produced muons can provide information with no radiation dose above the earth's background and proper detection of such cosmic ray-produced muons can be implemented in a way that is especially sensitive to good shielding materials. A muon detection system can be configured to perform tomography of a target object under inspection based on scattering of muons by the target object. The system can be configured to perform tomography to localize scattering (RC & LS). The tomographic position resolution can be expressed approximately as follows:

$$\Delta x = \theta_{RMS} L \quad \text{Eq. 1}$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta\theta}{\theta} = \frac{1}{\sqrt{2N}} \quad \text{Eq. 2}$$

where:

θ=the rms scattering angle,

N=number of cosmic ray-produced muons passing through a region of interest.

For example, the angular resolution for N=100 (corresponding to a 10×10 cm² resolution element after one minute of counting is Δθ=0.07θ.

Referring to the table of FIG. 10, this table illustrates theoretical energy loss rate (dE/dx) and radiation length (X) for various materials. One minute of counting distinguishes a 10 cm cube of iron from a 10 cm cube of lead at 6 standard deviations on the basis of their different values of X.

Tomographic methods, designed to construct an image or model of an object from multiple projections taken from different directions, can be implemented in the cosmic ray system to provide a discrete tomographic reconstruction of the volume of interest based on the data provided by the muons. In some implementations, Monte Carlo simulation techniques can be used to study applications and shorten scanning times. Other stochastic processing methods may also be used in implementing the muon tomographic imaging described in this application.

Figure 4:
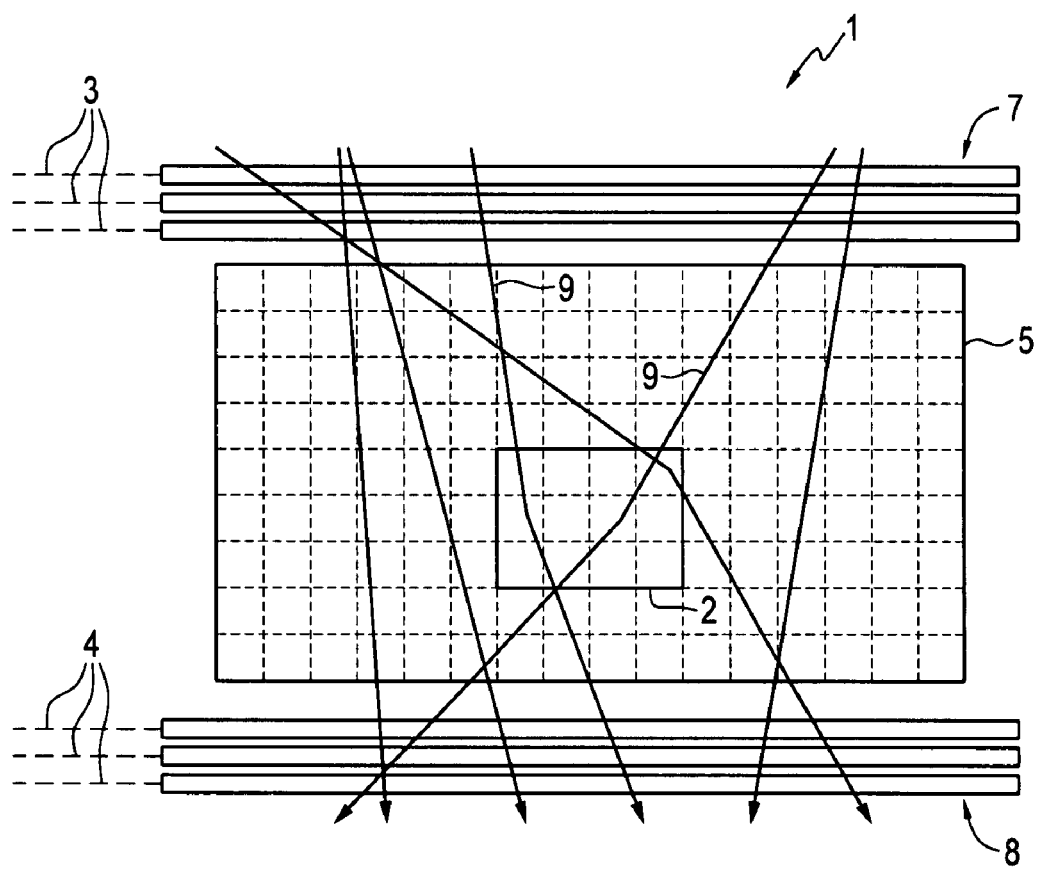
FIG. 4 illustrates an example of a detection system utilizing cosmic ray-produced muons to detect an object.
Figure 5:
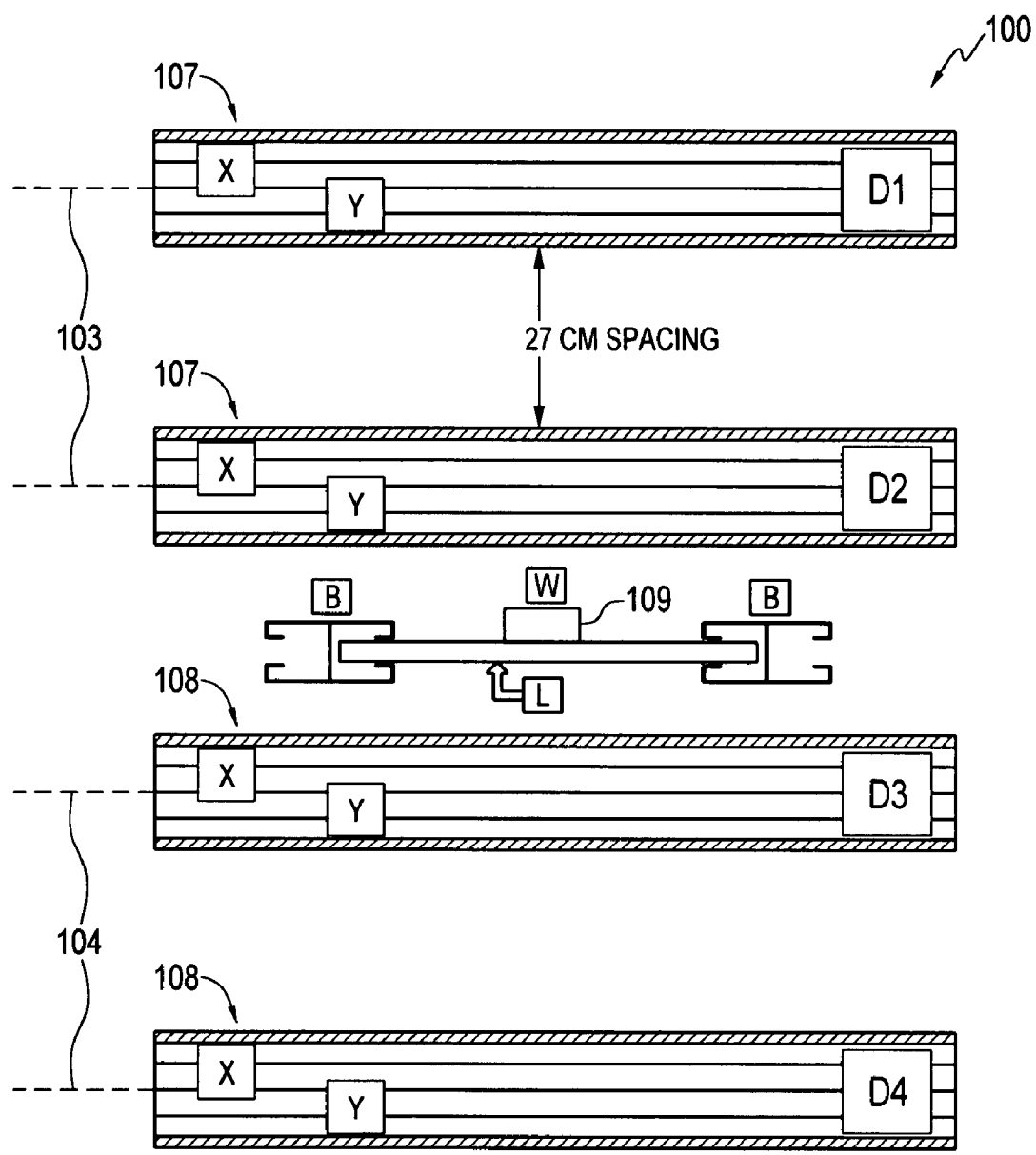
FIG. 5 illustrates a side view of another example of a detection system utilizing cosmic ray-produced muons to detect an object.
Figure 6:
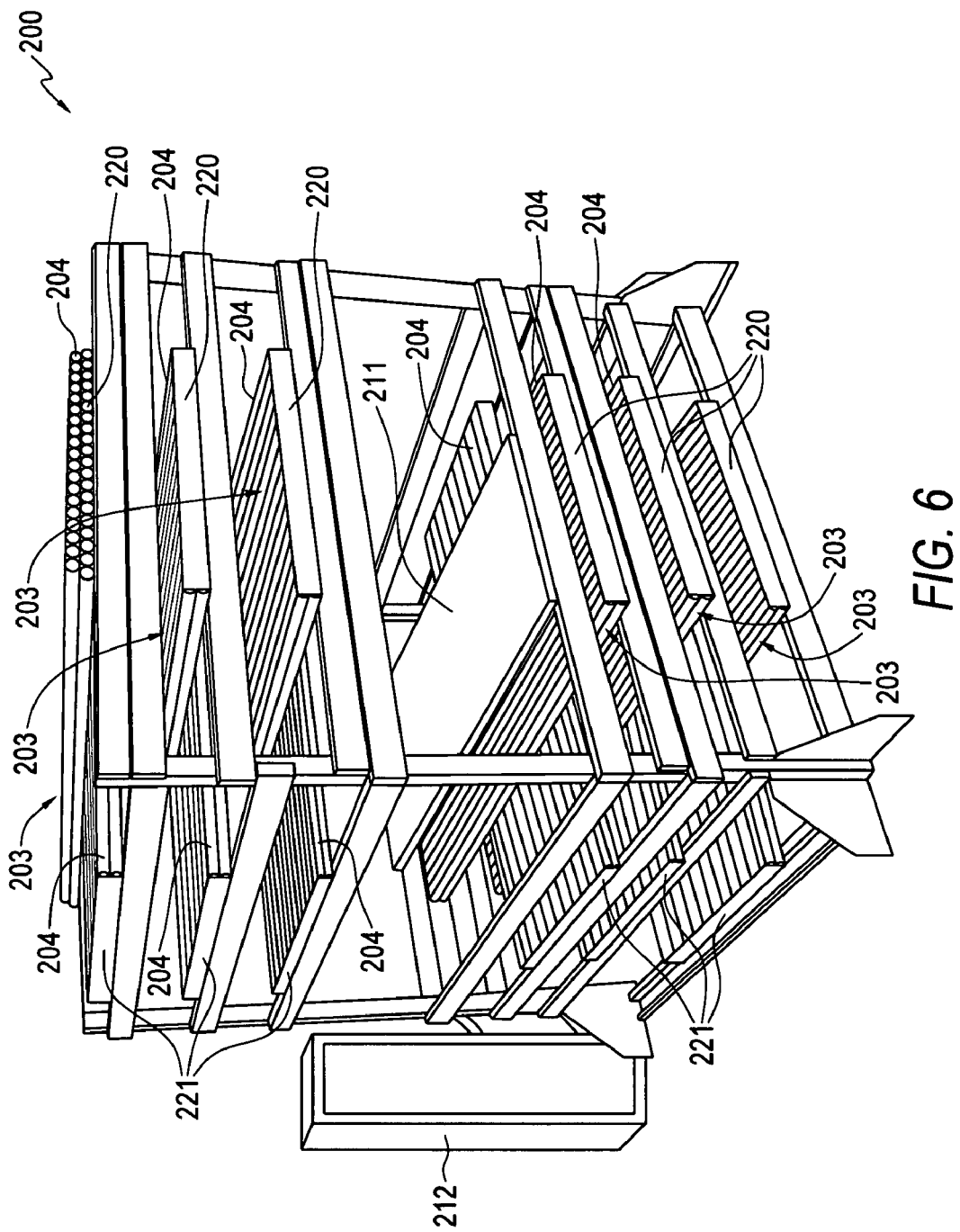
FIG. 6 illustrates a detailed perspective view of another example of a detection system utilizing cosmic ray-produced muons to detect an object.

The cosmic ray radiography function of the particle detection systems of the embodiments can be more readily understood with reference to examples of detection systems adapted to detect cosmic ray charged particles such as those shown in FIGS. 4-6.

Referring initially to FIG. 4, which illustrates a detection system utilizing cosmic ray-produced muons to detect an object, system 1 includes a set of two or more planes 3 of position-sensitive muon detectors 7 arranged above a volume 5 to be imaged for providing the position and angles (i.e., directions in the 3-D space) of incoming muon tracks 9. The muon detectors 7 are configured to measure the position and angles of incoming muon tracks 9 with respect to two different directions, e.g., in two orthogonal coordinates along x and y axes. Muons pass through the volume 5 where the object 2 may be located and are scattered to an extent dependent upon the material 2 occupying the volume through which they pass. Another set of two or more planes 4 of position-sensitive muon detectors 8 are configured to record outgoing muon positions and directions. The drift tubes in detectors 7 and 8 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks. The scattering angle of each muon is computed from the incoming and outgoing measurements.

A signal processing unit, e.g., a computer, is provided in the system 1 to receive data of measured signals of the incoming muons by the detectors 7 and outgoing muons by the detectors 8. This signal processing unit is configured to analyze the scattering of the muons in the volume 5 based on the measured incoming and outgoing positions and directions of muons to obtain a tomographic profile or the spatial distribution of the scattering density reflecting the scattering strength or radiation length within the volume 5. The obtained tomographic profile or the spatial distribution of the scattering density within the volume 5 can reveal the presence or absence of the object 2 in the volume 5. FIG. 4 shows drift tube detectors 7 and 8 are located on top and bottom sides of the volume 5. In some implementations, additional drift tube detectors can be implemented on sides of the volume 5 to form a box or four sided structure into which a package, a vehicle or cargo container can enter for scanning by the system.

The processing of measurements for cosmic ray-produced muons in a volume under inspection (e.g., a package, a container or a vehicle) by the processing unit for the system 1 in FIG. 4, and other systems described in this application can include reconstructing the trajectory of a muon through the volume 5, measuring the momentum of an incoming muon based on signals from the detectors 7, measuring the momentum of an outgoing muon based on signals from the detectors 8, and determining the spatial distribution of the scattering density of the volume 5. These and other processing results can be used to construct the tomographic profile and measure various properties of the volume 5.

For example, the reconstruction of the trajectory of a charged particle passing through a detector 7 or 8 having a set of drift tubes in FIG. 4 can include (a) receiving hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing muon based on signals from the detectors 7 or 8 in FIG. 4 can include, for example, (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume 5 in FIG. 4 can be determined from charged particle tomographic data by: (a) obtaining predetermined charged particle tomography data corresponding to scattering angles and estimated momentum of charged particles passing through object volume; (b) providing the probability distribution of charged particle scattering for use in an expectation maximization (ML/EM) algorithm, the probability distribution being based on a statistical multiple scattering model; (c) determining substantially maximum likelihood estimate of object volume density using the expectation maximization (ML/EM) algorithm; and (d) outputting reconstructed object volume scattering density. The reconstructed object volume scattering density can be used to identify the presence and/or type of object occupying the volume of interest from the reconstructed volume density profile. Various applications include cosmic ray-produced muon tomography for various homeland security inspection applications in which vehicles or cargo can be scanned by a muon tracker.

The tomographic processing part of the signal processing unit may be implemented in a computer at the same location as the detectors 7 and 8. Alternatively, the tomographic processing part of the signal processing unit may be implemented in a remote computer that is connected on a computer network such as a private network or a public network such as the Internet.

Thus, multiple scattering of cosmic ray-produced muons can be used to selectively detect high z-material in a background of normal cargo. Advantageously, this technique is passive, does not deliver any radiation dose above background, and is selective of high-z dense materials.

Referring to FIG. 5, which illustrates a side view of another detection system utilizing cosmic rays to detect an object, the system 100 has two planes 103 of muon detectors 107 located above the sample 109 and two planes 104 of muon detectors 108 located below the sample 109. In the system 100 the planes of muon detectors are separated by 27 cm spacings.

FIG. 6 illustrates a detailed perspective view of another charged particle detector 200 in which position sensitive detectors 203 are arranged above the sample holder plane 211 and position sensitive detectors 203 are arranged below the sample holder plane 211. Each set of position sensitive detectors comprises a first double-layer 220 of drift tubes 204 arranged in the X direction and a second double-layer 221 of drift tubes 204 arranged in the Y direction. In each of the layers 220, 221, the drift tubes 204 are arranged in two rows, offset by half a tube diameter from each other.

Drift tube modules 204 are operable to detect both cosmic ray muons and gamma rays. In the system of FIG. 6, the drift tube modules are 12 foot long aluminum drift tubes which are configured to measure the position and angle of incoming and outgoing muon tracks in X and Y coordinate directions. The aluminum in the detectors provides a considerable amount of mass in which gamma rays and energetic electrons are absorbed or scattered. The energetic electrons produced in these processes are detected locally in the drift tubes in the same way that more energetic cosmic rays are detected.

The tubes can be arranged in different ways. For example, the layers need not have to be 90 degrees from one another, but can be smaller non-zero angles. Also by way of example, the top layer could be at 0 degrees, middle layer at 45 degrees from the first, and a third layer 90 degrees from the first. This would allow resolution of multiple tracks that occur at the same instance of time.

Also, other position sensitive detector arrangements capable of scattering the charged particle passing therethrough and providing a total of at least three individual positional measurements can be adopted instead of the arrangement of detectors of FIG. 6. At least 3 position measurements are required so as to enable a line fit with a free parameter from which one can track the particle.

One example of the data acquisition electronics 212, operably coupled to the drift tubes, will now be described. Drift tubes of the detector system 200 of FIG. 6 are connected to respective electronic amplifiers (not shown) which increase the voltage of the deposited signal (associated with a cosmic ray muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number that the digital signal is registered to the nearest nanosecond by the time-to-digital-converters (TDCs) mentioned above. Each drift tube has its own front-end electronics and TDC.

The front-end electronics is built using hardware composed of off-the-shelf (OTS) parts. The TDC is OTS, and the units are built by Caen corporation in Italy. Each TDC unit (CAEN 767B) has the capability of 128 input channels (drift tubes in our case), and will store the time of the hit digitally. These units have a buffer which can hold about 32,000 hits. The TDCs are read-out about 5 times per second with a custom data-acquisition system (DAQ). The TDCs sit in a Versa Module Eurocard VME crate with a SIS 1100 controller, made by Struck Innovative Systeme GmbH (SIS), which provides the computer interface. The DAQ runs on a personal computer, with an optical cable to interface with the SIS 1100 to command the TDCs for the data transfer. Once the hit times and channel numbers are read out into the memory of the PC, the raw data is stored on hard drive, but the data is also processed to identify the cosmic ray events. The track data, and pertinent diagnostic data are also stored on the hard drive. The processing of measurements for cosmic ray-produced muons in a volume under inspection (e.g., a package, a container or a vehicle) by the data acquisition unit of the system of FIG. 6, or other signal processing unit linked thereto, can be similar to those explained above for the system of FIG. 4. For example, processing measurements may be reconstructing the trajectory of a muon through the volume, measuring the momentum of an incoming muon based on signals from the detectors, measuring the momentum of an outgoing muon based on signals from the detectors, and determining the spatial distribution of the scattering density of the volume.

Advantageously, system 200 can selectively detect high density shielding of radioactive material occupying the volume from multiple scattering of the cosmic ray-produced muons whilst also counting gamma rays emitted from the radioactive material. In addition to detecting high density materials, such as lead, gold, tungsten, uranium and plutonium, the system can be employed to detect medium density materials, such as steel, iron and copper, and also low density materials, such as water, plastic, concrete and aluminum, albeit with a somewhat lower accuracy than for high density materials.

Figure 7:
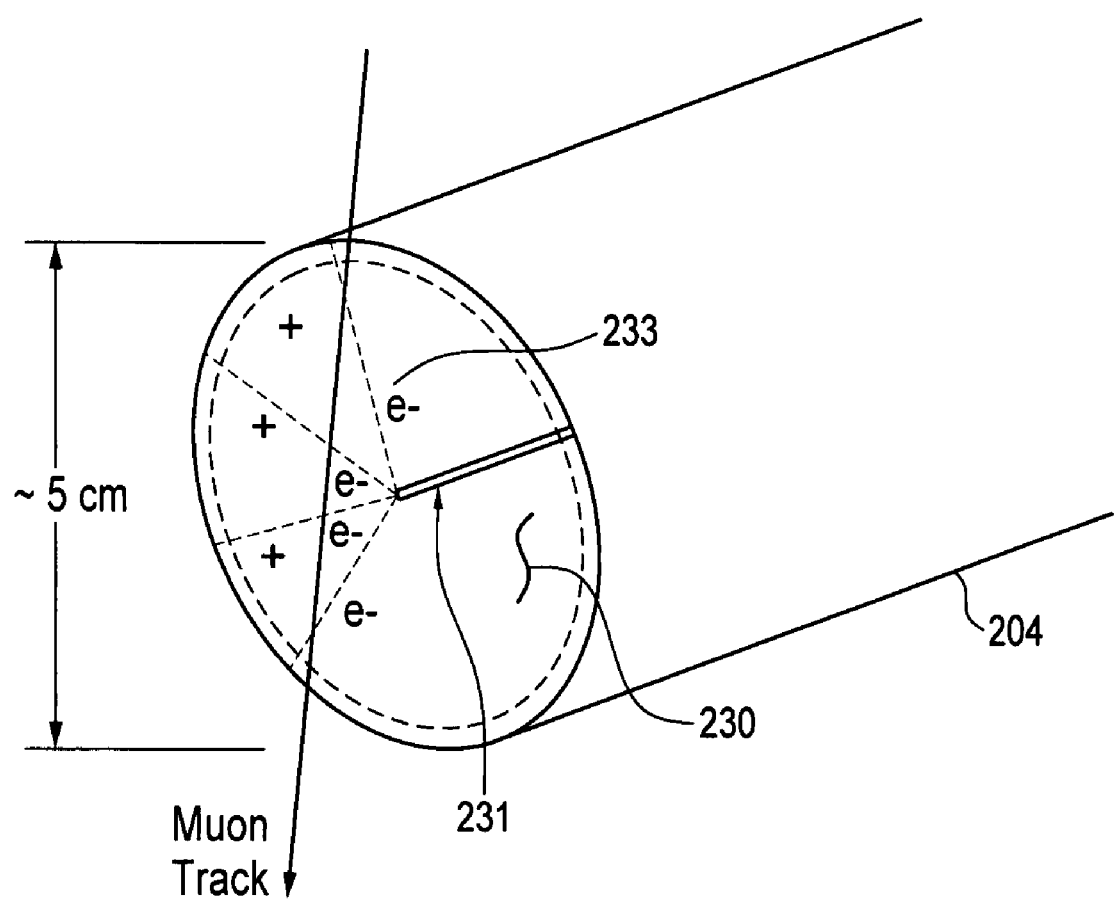
FIG. 7 illustrates a cross-sectional view of part of a drift tube module configured to detect cosmic ray charged particles and gamma rays.

A cross-sectional view of part of a typical drift tube module 204 is illustrated in FIG. 7. The drift tube module in this particular example is cylindrical and filled with a detector gas such as Argon-Isobutane 230 to enable detection of the cosmic ray-produced charged particles, such as muons. The system is configured to apply a positive high voltage of about +2-3 kV to a central anode wire 231 extending along the length of the cylindrical tube with the tube at ground so that a high-voltage static field is also present. When the charged particle interacts with gas atoms, many electrons 233 are liberated from those atoms along the charged particle's straight line path through a chord of the tube. The static field causes the "string" of electrons to drift toward the positively charged anode wire which is read-out electronically with TDCS (time-to-digital converters) of the data acquisition electronics 212.

Whilst in the drift tube of the illustrative embodiment of FIG. 7, the detector gas is Argon-Isobutane 230, other operating gas mixtures may be Argon/carbon dioxide or Argon/isobutane/carbon dioxide and can include hydrocarbons such as methane, propane, pentane and the like. An example of an operating gas mixture is 10% methane, 90% argon. Furthermore, non-flammable gas mixtures such as Argon-carbon-dioxide-tetrafluoromethane ($CF_4$) may alternatively be employed as the operating gas. Also, ethane or other gases may be adopted in the gas mixtures. For example, a mixture of 5% of ethane, 45% of CF4 and 50% of Argon is a suitable non-flammable operating gas. Inert gases other than Argon can be used in the gas mixture.

Also, whilst the drift tube of FIG. 7 is manufactured from aluminum, other materials such as carbon composite with internal conductive coatings can be adopted instead of aluminum. The drift tubes need not have circular cross-sections. For example, the drift tubes may be constructed from aluminum extrusions with multiple, non-circular cross-sections.

Alternatively, drift cells other than drift tubes can be adopted such as for example triangular shaped drift cells.

Figure 8:
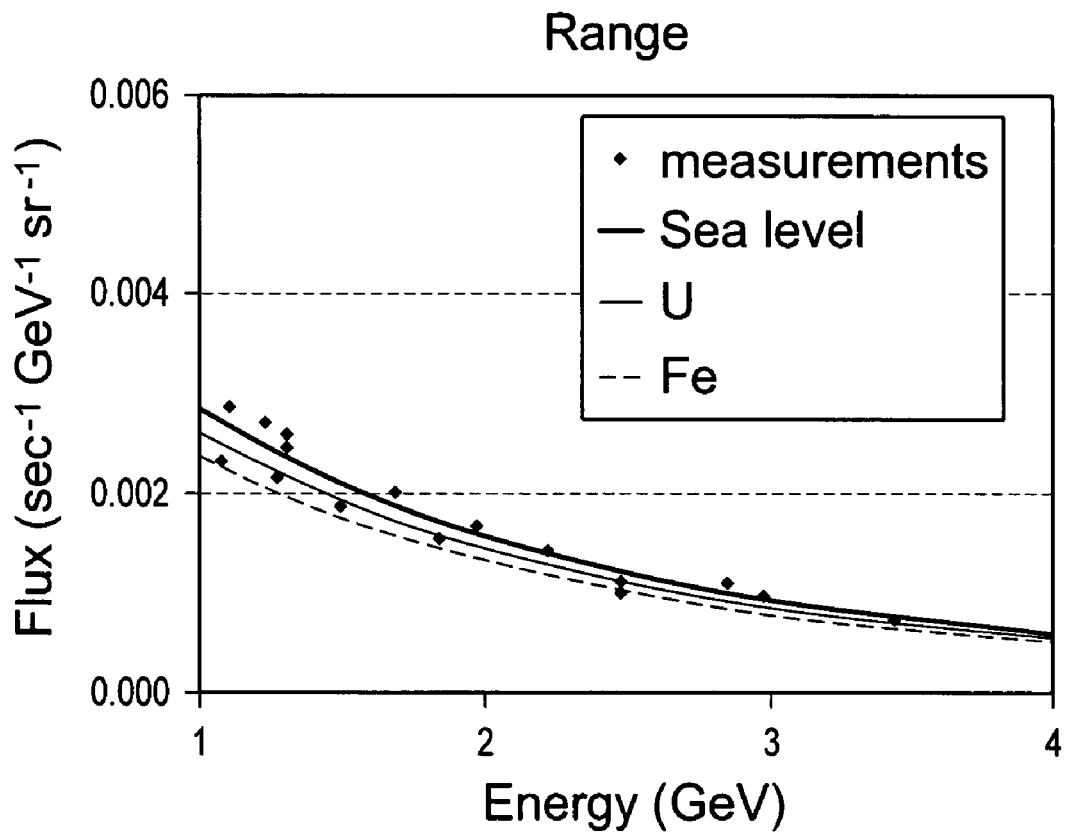
FIGS. 8 and 9 respectively illustrate typical experimental range data and multiple coulomb scattering theoretical results of measuring 1000 cm$^2$ of uranium for 1 minute with a cosmic ray system.
Figure 9:
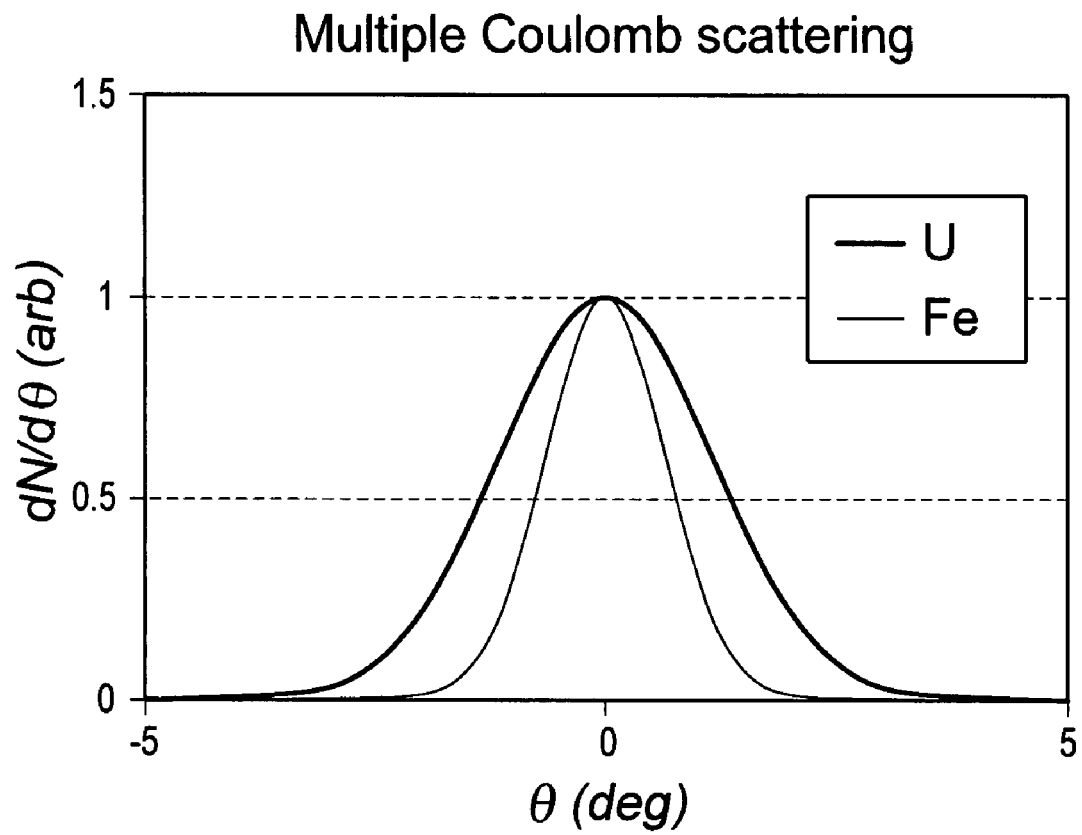

FIGS. 8 and 9 respectively illustrate exemplary experimental range data and multiple Coulomb scattering theoretical results of measuring 1000 $cm^3$ of uranium for 1 minute with a cosmic ray-produced muon detection system. These measurements and computations demonstrate that charged particle (muon) tomography is much more sensitive than the range radiography previously employed in searches for hidden chambers in an Egyptian pyramid and measurement of geological overburden.

Figure 11:
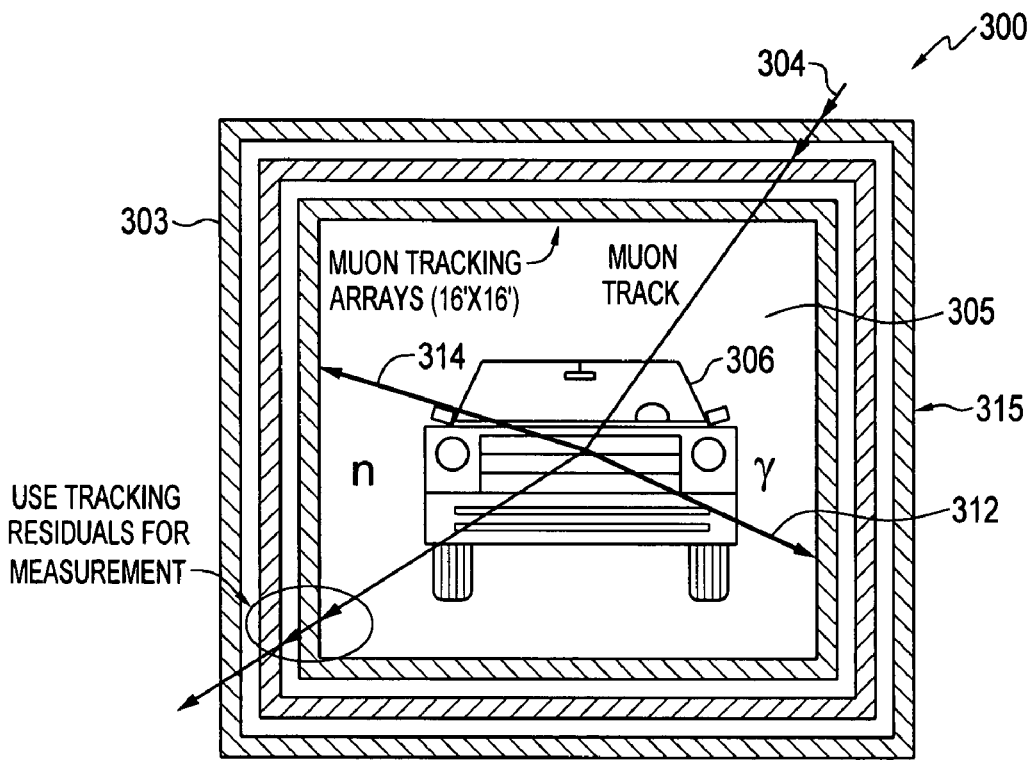
FIG. 11 illustrates a particle detection system adapted and arranged to monitor cargo in vehicles and containers at ports and border crossings according to one embodiment.

FIG. 11 illustrates a particle detection system 300 adapted and arranged to monitor cargo in vehicles and containers at ports and border crossings according to one embodiment. As will be explained in more detail below, the particle detection system 300 uses a muon tomography system with a plurality of detector drift tubes 303 configured to track cosmic ray-produced muons 304 scattered by the cargo or contents of a vehicle 306 occupying the volume 306 and configured to concurrently detect any neutrons 314 emitted from the vehicle contents. The system 300 can be employed for inspecting occupied vehicles at border crossings for nuclear threat objects which might range from fully assembled nuclear weapons to small quantities of highly shielded nuclear materials. The system 300 can be used to pass innocent vehicles in less than 30 seconds, detect several Kgs of highly enriched uranium (HEU) in less than 60 seconds (shielded or unshielded) and detect plutonium or HEU nuclear devices in less than 60 seconds (shielded or unshielded).

Both plutonium and weapons grade uranium are sources of neutrons either from the amplification of the natural neutron background ("fission chains") or from individual spontaneous fissions within the material. The particle tracking system 300 is similar in construction to the system 200 of FIG. 6 and in the system 300 the drift tubes are arranged to form a box or four sided structure 315 around the volume to be scanned 305. Notably, the drift tubes are designed to include a neutron sensitive medium to enable the drift tubes to concurrently detect any neutrons emitted from the vehicle 306.

The neutron sensitive medium can include Helium-3, Boron or Lithium and can be in solid, liquid or gas form. A hydrogenous material, such as hydrogenous organic materials (e.g., Polyethylene and paraffin) or water, can be used to trap and confine neutrons so that they pass through the drift cells multiple times and are isolated from the material or devices being scanned. Such a hydrogenous material can also moderate the neutron energy by slowing down the neutrons to increase their interaction cross-section by very large factors. Boron or a boron compound may be enriched in the isotope boron-10 and lithium or a lithium compound can be enriched in the isotope lithium-6. The operating gas of the drift tubes can comprise a mixture of argon and at least one gas selected from the group consisting of carbon dioxide, isobutane, tetrafluoromethane and ethane to enable counting of gamma rays such that, in use, the system can additionally detect any radioactive sources occupying the volume from gamma rays emitted therefrom.

The drift tubes can also include a gamma ray scattering solid material to enable detection of gamma rays. Helium-3 can be added to any of these gases to permit simultaneous neutron detection by the same drift tube. If the drift tube contains only argon and tetrafluoromethane then boron trifluoride, possibly advantageously enriched in the isotope boron-10, could be added to permit simultaneous neutron detection by the same drift tube. Alternatively, neutron detectors could utilize drift tubes optimized for that purpose, distinct from the tubes for detection of charged particles (muons).

The detection of neutrons can be achieved in many ways. In the illustrative embodiment of the detector of FIG. 11, the operating gas of the tracking drift tubes 303 includes a partial pressure of Helium-3 (3He) which constitutes the neutron sensitive medium to enable the drift tubes to concurrently detect any neutrons. For example, the operating gas can be a combination of Helium-3 (3He), ethane, tetrafluoromethane and argon. The detector can also use Helium-3 (3He) in combination with other different sets of fill gases.

This combined use of cosmic muon ray detection and neutron detection function is illustrated in FIG. 11. The neutrons are seen in the normal electronics as much larger pulses than those of the muons. This is due to the high energy loss rate of the protons produced by neutron interaction with helium-3 or of the massive charged particles produced by neutron interaction with boron-10 or lithium-6. The drift tubes 303 can be sealed further to decrease cost and complexity of the system by eliminating the need for a gas handling system. The system can also be used to detect gamma rays 312 in the same manner as the system 200 of FIG. 6.

Using the drift tubes 303 to both passively count neutron and optionally gamma particles 314 emitted from the vehicle 306 and track the scattered cosmic ray-produced charged particles 304 (muons) enables the system to function as an efficient monitor of radiation emitted by threat objects in addition to cosmic ray imaging providing a more compact and cost effective detector system to look for nuclear devices and materials at border crossings and ports.

Addition of the neutron sensitive medium to the tracking drift tubes 303 provides efficient selective neutron detection with no impact on muon tracking and allows detection of unshielded neutron sources in vehicles and containers. This has three main benefits over using separate systems to detect neutrons and radiograph vehicles. Firstly, the single detector system is cheaper than several systems. Secondly, the system takes up less space which is limited. Thirdly, the detector system can provide positioning information about the neutron source, independent of the muon signal.

A method of operating the particle detection system 300 of FIG. 11 according to one embodiment involves detecting with the drift tubes 303 incoming and outgoing cosmic ray-produced charged particles 304 together with any gamma rays 312. The multiple scattering of the charged particles are then computed to selectively detect material, particularly high density material, occupying the volume 305. Any neutron particles emitted from the volume 305 are counted by the data acquisition electronics (not shown) to detect if any unshielded neutron source is occupying the volume. Any gamma rays 312 emitted from the volume can also be counted by the data acquisition electronics to detect if any radioactive source is occupying the volume 305.

Types of gas that can be used as the neutron sensitive medium include boron trifluoride (BF3), Helium-3 (3He), Boron and a Boron compound, Lithium and a lithium compound, or other elements used in the detection of neutrons. The neutron sensitive medium included in the drift tubes can be in form of a gas, solid liquid. For example, the neutron sensitive medium can be a thinly coated lithium, a conductive compound of lithium or boron on the inside of the tube in conjunction or without Helium-3 (3He) in the detector gas. The lithium or boron may be advantageously enriched in the isotopes lithium-6 or boron-10, respectively, for a neutron sensitive medium.

Figure 14:
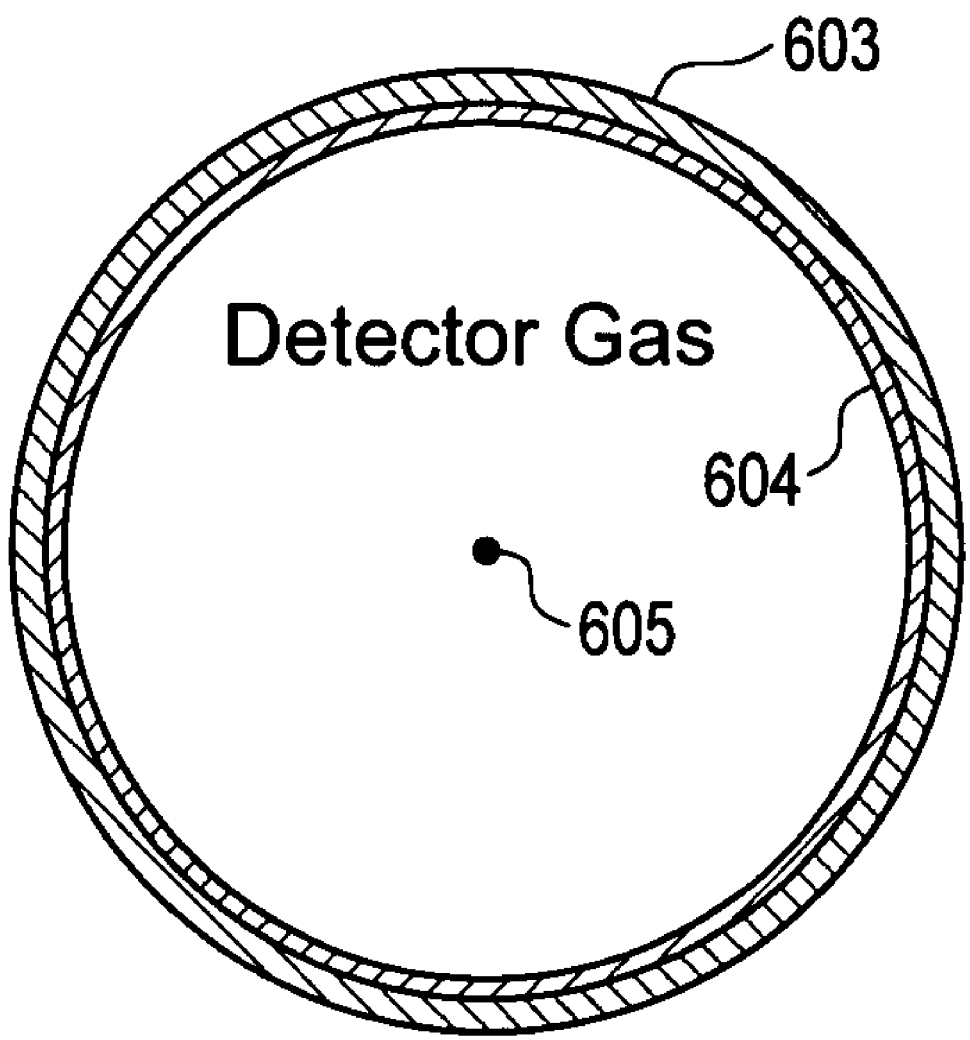
FIG. 14 which illustrates a cross-section of a neutron sensitive drift tube according to one embodiment.

Alternatively or additionally, the neutron sensitive medium can be a solid layer or region of neutron sensitive material for example as shown in FIG. 14, which illustrates a cross-section of a neutron sensitive drift tube according to one embodiment. Drift tube 603 having anode wire 605 includes a conductive neutron sensitive layer 604 disposed on the interior wall of the drift tube. The neutron sensitive layer can be for example a conductive compound of lithium or boron. The neutron sensitive layer 604 can be used in conjunction with or without helium-3 (3He) in the detector gas.

In alternative embodiments, the drift tubes or other drift cells including neutron sensitive material need not be arranged to form a four sided structure as shown in FIG. 11. For example, the neutron sensitive drift tubes can be arranged to form a top and bottom side structure such as that of the detector system 200 of FIG. 6.

In yet another alternative embodiment, a particle detection system (not shown) is provided which is identical to that of the particle detection system 300 of FIG. 11 with the exception that the system also includes a gamma ray and/or neutron source within the apparatus to enable active rather than only passive interrogation of the vehicle and thereby provide a detectable increase in the gamma ray and/or neutron counting rate.

Figure 12:
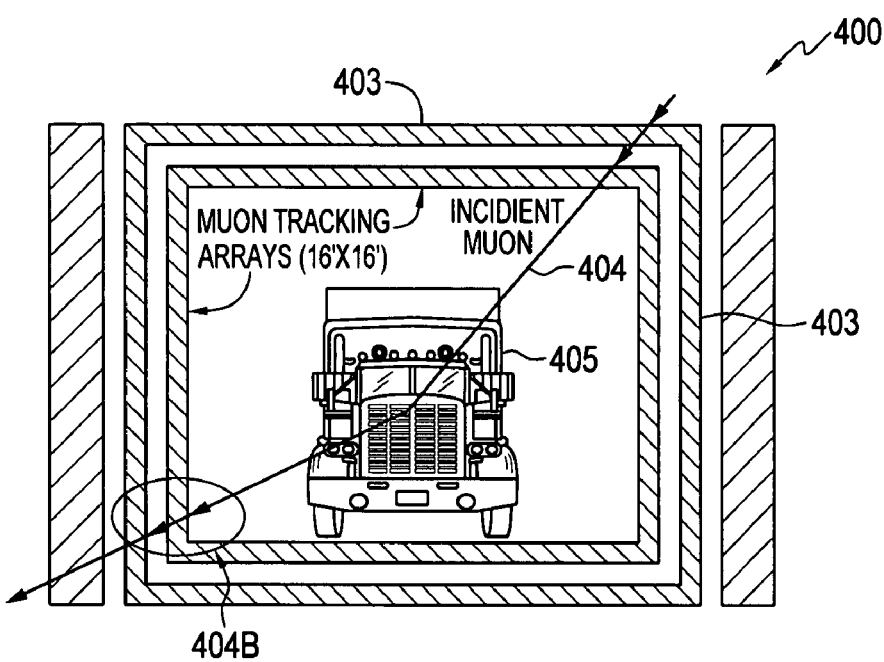
FIG. 12 illustrates a particle detection system adapted and arranged to monitor cargo in vehicles and containers at ports and border crossings according to another embodiment.

A particle detection system according to another alternative embodiment is illustrated in FIG. 12. System 400 is similar to the system 300 of FIG. 11 in that it is configured to both passively count gamma and/or neutron radiation emitted from the vehicle and track the scattered cosmic ray-produced charged particles 404. In one implementation, for example, the drift tube detectors arrays 403 can be sufficiently long to accommodate for interrogation of a large cargo or vehicle (e.g., a truck) 405 (e.g., 16 feet in length). In order to obtain major gains in rate, the solid angle is increased by filling out the drift tube detectors 403. Furthermore, the system is configured to use tracking residuals 404B for momentum measurements.

Figure 13:
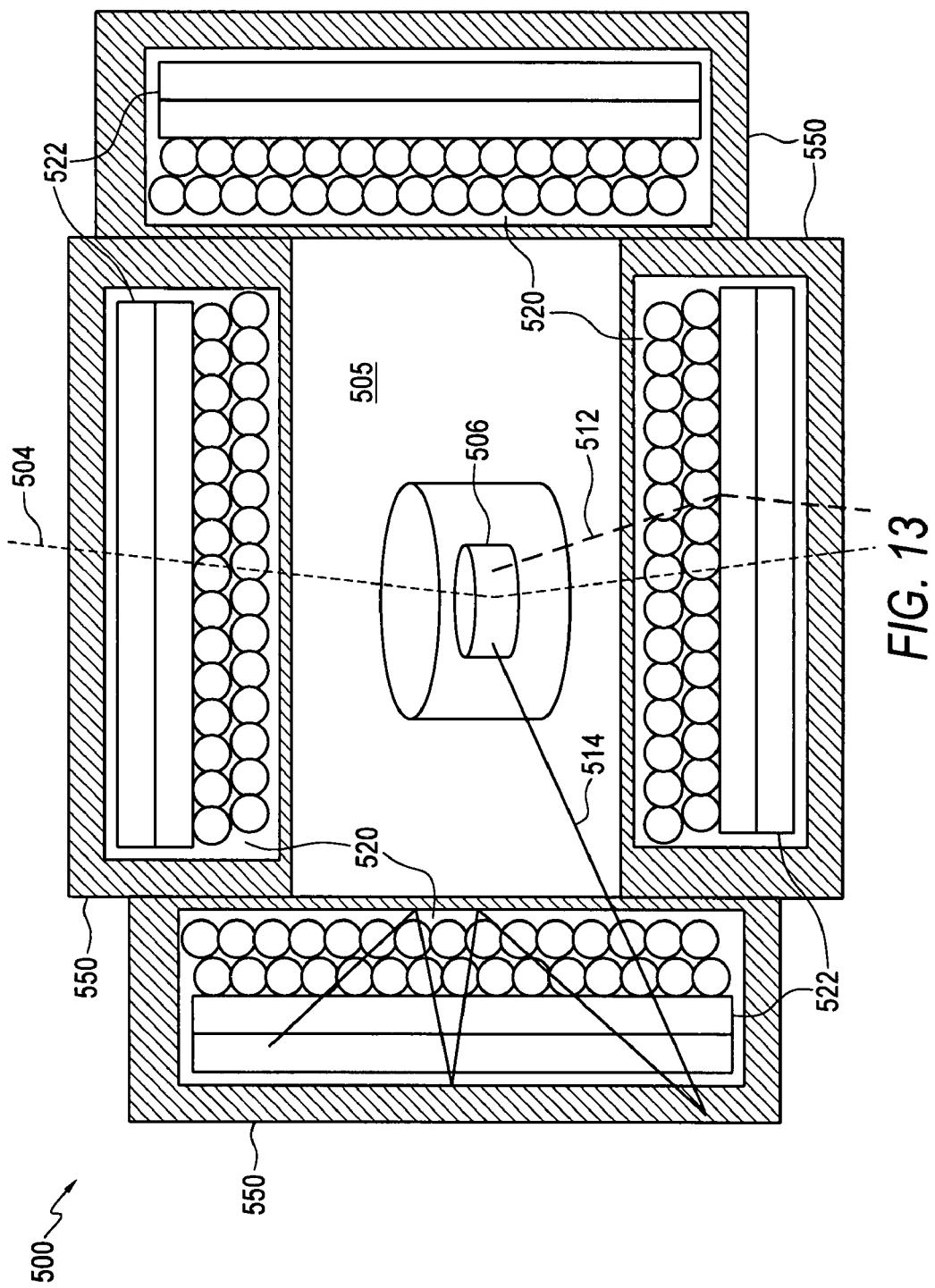
FIG. 13 illustrates a particle detection system with enhanced neutron detection efficiency according to yet another embodiment.

FIG. 13 illustrates a cross-section view of a particle detection system 500 according to yet another embodiment. The particle detection system 500 includes various features used in the system 300 of FIG. 11. Notably, the particle detection system 500 implements a hydrogenous material 550 in the drift tube box structure to trap and moderate neutrons in the apparatus so that neutrons pass through the neutron sensitive detectors several times. This design can be used to increase the neutron detection sensitivity and efficiency of the detector. For the sake of clarity, FIG. 13 shows only single sets of drift tube detectors on each side, each set of drift tube detector having X and Y drift tube modules 520,522. However, in practice, the detector system 500 can have three sets of drift tube detectors on each side in the same manner as the detector system 300 of FIG. 11.

FIG. 13 depicts an object 506 to be scanned, which is disposed in volume 505, in conjunction with examples of a cosmic ray-produced muon path 504, which passes through the detector system and is deflected by the object 506 and a gamma path 512 and neutron path 512 from the object 506. In the detector system 500 of FIG. 13, all of the X and Y detector tube modules 520, 522 in each set are enclosed in hydrogenous material 550 to achieve efficient neutron detection.

The hydrogenous material is used to slow down, or thermalize the neutrons to energies low enough near thermal energies so that Helium-3 (3He) or other neutron sensitive medium such as boron, lithium, isotopically enriched in boron-10 or lithium-6, or their compounds can efficiently detect the neutrons. As indicated by the example neutron path 514 in FIG. 13, the hydrogenous material surrounds the detectors to trap and then reflect the thermalized or moderated neutrons in the detector drift tube region causing multiple passes through the detector tubes 520,522. However, not all the detectors need be enclosed. Only those tube layers that have neutron sensitivity and for which an increase in detection efficiency is required need be enclosed by the hydrogenous material. For example, a plane of hydrogenous material can be incorporated into the center of the middle set of drift tubes so that it acts as a container for neutrons and improves the neutron efficiency for a neutron counting system inside of the middle plane. Furthermore, drift tubes with or without neutron enclosures need not be arranged on all four sides as shown in FIG. 13. For example, the drift tubes can be arranged on top and bottom sides only in the same manner as the drift tubes of the detector system 200 of FIG. 6 Neutron sensitive tubes may be arranged on any or all sides.

The hydrogenous material 550 can be a polyethylene enclosure 550 which increases the count rate by thermalizing high energy neutrons and trapping thermal neutrons in the detector. Alternatively, the hydrogenous material 550 can be water, or other hydrogenous materials capable of thermalizing neutrons.

In addition to increasing the neutron detection efficiency of the detector, enclosing the drift tubes or other drift cells in hydrogenous material traps neutrons within the enclosure so that the neutrons are not absorbed by the object being scanned. It is also possible to reconstruct the neutron source position to some extent using detector enclosed in a hydrogenous material.

Additionally or alternatively, hydrogenous material may be used in other parts of the system without neutron sensitivity to reflect neutrons into the sensitive region. Hydrogenous materials on the exterior of the system helps shield external neutrons from detection, in addition to thermalizing and trapping the neutron originating on the inside. The addition of a neutron absorbing medium like boron in the outer most layer will further lower the number of external neutrons entering the detector. In this case, the outer most layer of the detector might be boreated polyethylene, with a layer of non-boreated polyethylene inside of this.

The particle detection system 500 of FIG. 13 can also be used as a neutron detector only to detect neutrons and optionally gamma rays without necessarily having to detect charged particle muons.

The aforementioned illustrative embodiments describe cosmic ray produced muon tomography systems and techniques and demonstrate that the combination of cosmic ray produced muon tomography with passive or active counting therefore provides a robust detector for nuclear threats. Conventional radiography alone is defeated by packaging nuclear material in packages too small to be resolved by the radiography.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The invention claimed is:

1. A particle detection system comprising
a cosmic ray charged particle tracker having a plurality of particle detectors, said particle detectors comprising drift cells arranged on sides of a volume to be scanned to enable tracking of incoming and outgoing charged particles passing through said volume, at least some of said drift cells including a medium sensitive to neutron emission from nuclear material such that pulses read from said drift cells are larger for neutrons than for cosmic ray charged particles and wherein said particle detectors detect multiple scattering of said cosmic ray charged particles passing through said volume and concurrent neutron emission from nuclear material within said volume; and
wherein, in use, said system selectively detects one or more materials or devices occupying said volume from multiple scattering of said charged particles and concurrently detects one or more nuclear materials occupying said volume from neutron emission therefrom.

2. The system of claim 1, wherein said medium sensitive to neutron emission from nuclear material comprises gas and/or material.

3. The system of claim 1, wherein said medium sensitive to neutron emission from nuclear material comprises helium-3 (3He), boron or lithium.

4. The system of claim 1, further comprising a hydrogenous material thereby causing said neutrons to pass through said drift cells multiple times to be moderated and to be isolated from the material or devices being scanned.

5. The system of claim 4, wherein said hydrogenous material comprises water, polyethylene, or another organic hydrogenous material.

6. The system of claim 1, further comprising a hydrogenous material carried on at least one of an exterior and interior of said system such that neutrons are reflected towards said neutron sensitive drift cells.

7. The system of claim 1, wherein said drift cells on each of said sides comprise drift tubes arranged to allow at least three charged particle positional measurements in a first direction and at least three charged particle positional measurements in a second direction which may be orthogonal or non-orthogonal to the first direction.

8. The system of claim 1, wherein said drift cells also carry a gamma ray scattering material to enable detection of gamma rays such that, in use, said system can additionally detect any radioactive sources occupying said volume from gamma rays emitted therefrom.

9. The system of claim 1, wherein said drift cells are further adapted and arranged on surrounding sides of said volume such that said drift cells form a box or four sided structure into which an object is placed for scanning by said system.

10. The system of claim 1, wherein said drift cells are adapted and arranged on surrounding sides of the volume such that the drift cells form a box or four sided structure.

11. A particle detection system comprising
a cosmic ray-produced muon tracker having a plurality of muon detectors, said muon detectors comprising drift cells arranged at least above and below a volume to be scanned to enable tracking of incoming and outgoing muons, at least some of said drift cells including a medium sensitive to neutron emission from nuclear material such that said muon detectors detect said muons passing through said volume and concurrent neutron emission from nuclear material occupying said volume and, wherein, in use, said system detects shielding or other objects occupying said volume from multiple scattering of said muons passing through said volume and concurrently detects nuclear material occupying said volume from neutron emission therefrom.

12. The system of claim 11, wherein said drift cells comprise gas-filled drift tubes.

13. The system of claim 12, wherein the medium sensitive to neutron emission from nuclear material and included in the neutron sensitive gas-filled drift tubes comprises at least one of partial pressure of gas and a layer of conductive material disposed in the interior of said drift tubes.

14. The system of claim 12, wherein said drift tubes comprise aluminum drift tubes.

15. The system of claim 12, further comprising a hydrogenous material enclosing at least some of the neutron sensitive drift tubes thereby causing said neutron particles to be moderated and pass through said neutron sensitive drift tubes multiple times and to be isolated from the material or devices being scanned.

16. The system of claim 12, wherein said drift tubes are fabricated from a gamma ray compton scattering electron producing material such that, in use, said system can additionally detect any radioactive sources occupying said volume from gamma rays emitted therefrom.

17. A method of particle detection comprising
arranging a plurality of cosmic ray charged particle drift cells on sides of a volume to be scanned to include a medium sensitive to neutron emission from nuclear material such that pulses read from said drift cells are larger for neutrons than for cosmic ray charged particles to enable concurrent detection of said neutrons;
detecting with said drift cells multiple scattering of said charged particles passing through said volume and concurrent neutron emission from a nuclear material within said volume;
detecting any high density material occupying said volume from multiple scattering of said charged particles passing through said volume; and
detecting nuclear material occupying said volume from neutron emission therefrom.

18. The method of claim 17, wherein arranging a plurality of cosmic ray charged particle drift cells on sides of a volume to be scanned comprises arranging a plurality of gas-filled drift tubes on said sides of said volume; and wherein including said medium sensitive to neutron emission from nuclear material comprises adding a partial pressure of gas sensitive to said neutron emission to the operating gas of said gas-filled drift tubes and/or disposing a layer of material sensitive to said neutron emission_in said gas-filled drift tubes.

19. A neutron sensitive drift tube for use in a combined cosmic ray charged particle and neutron detection system; comprising:
a gas tube;
an operating gas confined in the gas tube and selected to enable detection of cosmic ray charged particles; and
a medium sensitive to neutron emission from nuclear material, said medium being carried thereon such that pulses read from said drift tube are larger for said neutron emission than for said cosmic ray charged particles to enable detection of cosmic ray charged particles and concurrent neutron emission from nuclear material.

20. The drift tube of claim 19, wherein said medium sensitive to neutron emission from nuclear material comprises at least one of a partial pressure of gas and a layer of material carried on an inner surface of said drift tube.

21. The drift tube of claim 19, wherein said medium sensitive to neutron emission from nuclear material comprises helium-3 (3He), boron, a compound of boron, a compound of lithium.

22. A particle detection system comprising
a first set of particle detectors located on a first side of an object holding area to measure incident charged particles towards the object holding area and to respond to a neutron emission from nuclear material to measure neutrons; and
a second set of particle detectors located on a second side of the object holding area opposite to the first side to measure outgoing charged particles exiting the object holding area and to respond to a neutron emission from nuclear material to measure neutrons,
wherein each particle detector comprises a charged particle sensitive material to measure charged particles and a material sensitive to neutron emission from nuclear material to measure neutrons and is operable to detect both charged particles and concurrent neutron emission from nuclear material.

23. The system of claim 22, wherein said charged particles comprise muons.

24. The system of claim 23, wherein:
each particle detector comprises a drift tube filled with a mixture of a muon sensitive gas and a gas sensitive to neutron emission from nuclear material,
each of the first and second sets of particle detectors is configured to be a set of position sensitive detectors to measure positions and directions of received muons, and
wherein the system comprises a signal processing unit to process measured signals from the first and second sets of particle detectors to produce a tomographic profile of one or more objects in the object holding area.

25. The system of claim 24, further comprising additional sets of said drift tubes adapted and arranged on surrounding sides of the object holding area such that said drift tubes form a box or four sided structure.

26. The system of claim 23, wherein
each particle detector comprises a drift tube filled with a mixture of a muon sensitive gas, and a solid material sensitive to neutron emission from nuclear material, said solid material being located inside the drift tube,
each of the first and second sets of particle detectors is configured to be a set of position sensitive detectors to measure positions and directions of received muons, and
wherein the system comprises a signal processing unit to process measured signals from the first and second sets of particle detectors to produce a tomographic profile of one or more objects in the object holding area.

27. The system of claim 23, wherein:
each of the first and second sets of particle detectors comprises drift tubes arranged to allow at least three charged particle positional measurements.

* * * * *